United States Patent [19]
McGovern

[11] 3,992,856
[45] Nov. 23, 1976

[54] STIRRUP PAD

[75] Inventor: A. James McGovern, Los Gatos, Calif.

[73] Assignee: Lawrence Peska Associates, Inc., New York, N.Y. ; a part interest

[22] Filed: Aug. 7, 1975

[21] Appl. No.: 602,819

[52] U.S. Cl. .................................................... 54/1
[51] Int. Cl.² ........................................ B68B 1/00
[58] Field of Search ............ 54/47, 1; 269/322, 328; 150/52 R, 52 G; 297/219, 220; 5/335, 327 R, 327 B, 334 C, 334 R

[56] References Cited
UNITED STATES PATENTS

| | | | |
|---|---|---|---|
| 2,732,269 | 1/1956 | Astroff.................................. | 269/328 |
| 2,804,632 | 9/1957 | Ford..................................... | 5/334 C |
| 2,911,657 | 11/1959 | Streeter................................ | 5/327 R |
| 3,273,175 | 9/1966 | Anderson et al. .................. | 5/335 X |

Primary Examiner—Louis G. Mancene
Assistant Examiner—Jack Q. Lever

[57] ABSTRACT

A pad adapted to be fitted about the contour of a stirrup used by the medical profession in making patient examinations.

5 Claims, 3 Drawing Figures

STIRRUP PAD

BACKGROUND OF THE INVENTION

The invention relates to a pad for the stirrups found on a patient examination table. More particularly, the invention relates to a pad that is especially adapted to provide the patient's foot with a degree of comfort not heretofore available by merely placing the foot in the metal stirrup.

The prior art relating to stirrup pads teaches those that are applied to stirrups on a horse saddle. Moreover, the pads do not cover the stirrup but merely provide for a grip portion adapted to engage the lower surface of the shoe of the rider. For example, U.S. Pat. Nos.: 222,556; 376,526; 1,639,073; 2,187,983; and others.

SUMMARY OF THE INVENTION

It is accordingly an object of the instant invention to provide for a cover for the stirrups of a patient examination table.

It is another object of the invention to provide for a cover that is easily adjustable to fit a variety of different size stirrups.

It is a further object to provide for a durable yet inexpensive cover.

Figure 1:
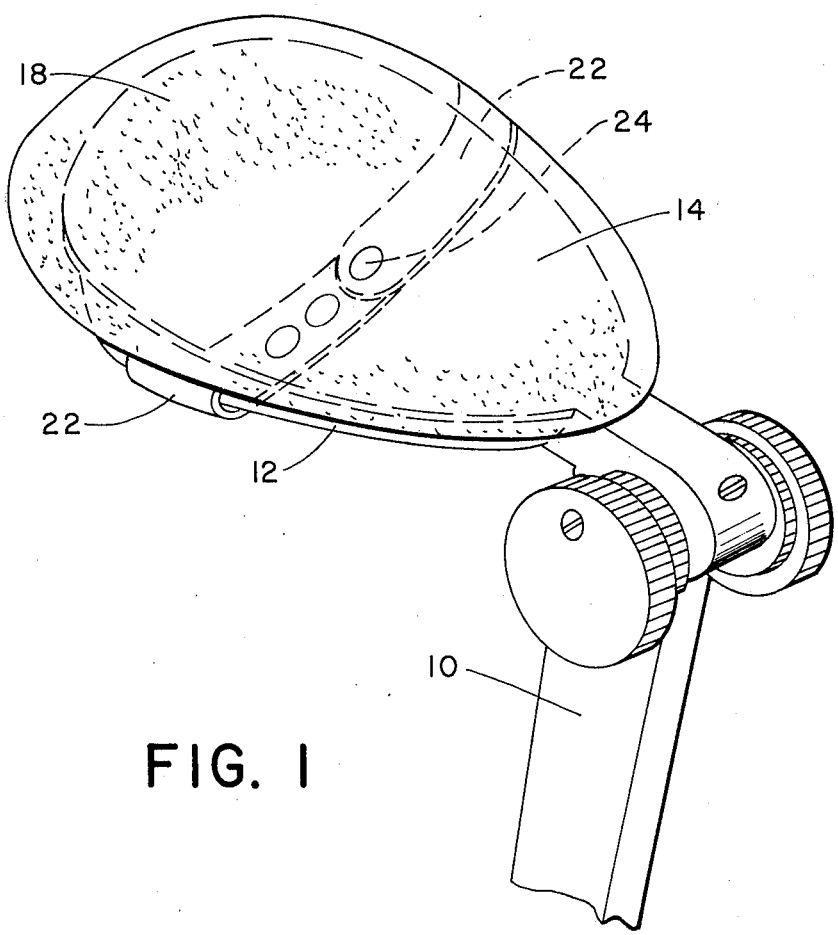
Figure 2:
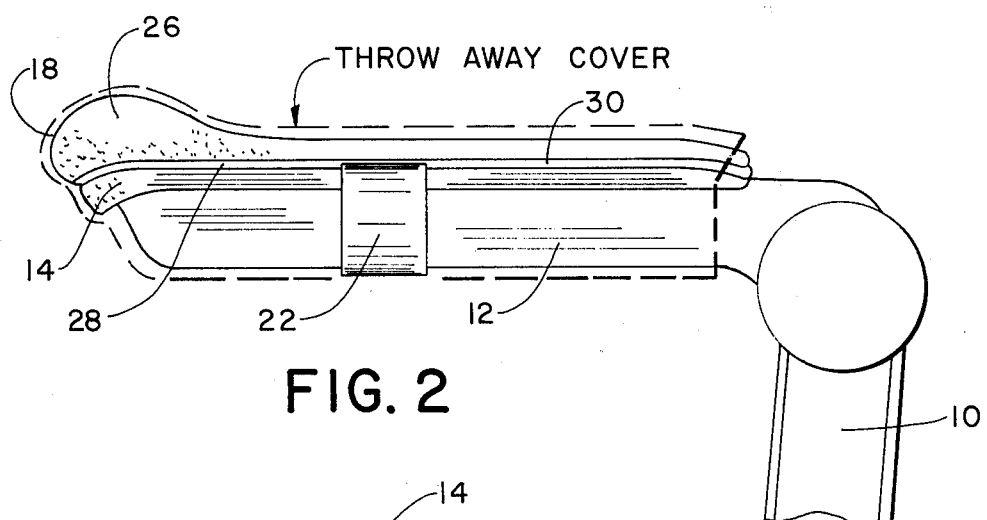
Figure 3:
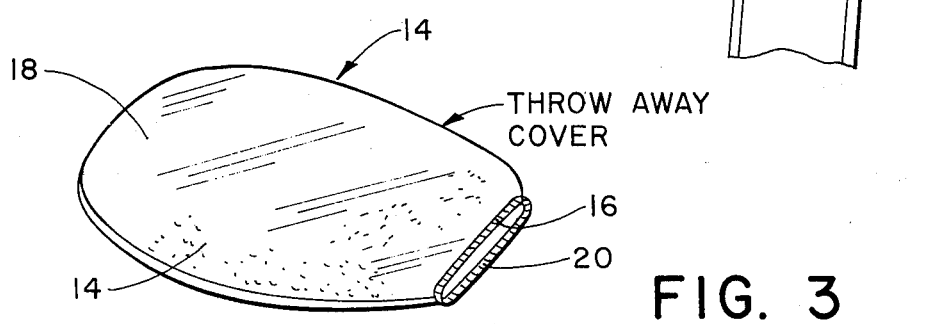

These and other objects of the invention will become more apparent from the following detailed disclosure and claims and by reference to the accompanying drawings, in which:

FIG. 1 is a top plan view of the cover on a stirrup;
FIG. 2 is a side elevational view thereof; and
FIG. 3 is a top plan view of the cover.

Broadly speaking, the instant invention includes the provision of a cover pad for the stirrup of a patient examination table, comprising a sleeve open at one end and defining a mouth for receiving the stirrup therein, at least the distal closed end of the sleeve being out of planar alignment with the remaining surface of the sleeve, a pair of straps disposed on the sleeve and adapted to contact one another whereby the sleeve may be tightened about the stirrup and fastening means disposed on the straps for securely engaging the same.

DETAILED DISCLOSURE

Referring more particularly to the drawings, there is shown the frame means 10 of the metal stirrup 12 containing member of a patient examination table. The stirrup 12 is generally somewhat oval in shape and defines a central aperture into which the heel of the foot is placed. The instant cover 14 comprises a substantially oval shaped sleeve 14 open at one end and defining a mouth 16 therein for insertion of the stirrup 12 thereinto. The sleeve 14 will preferably be constructed of a durable yet pliable material such as terry cloth, non woven material such as a paper byproduct or the like. If desired, the outer surface of the sleeve can include a vinyl substance to facilitate the cleaning of the same. In the preferred embodiment the sleeve is designed such that at least one distal end 18 thereof, e.g., opposite the mouth 16 will be out of planar alignment with the balance of the sleeve 14 thereby providing a greater degree of comfort for the heel of the foot. The distal end near the mouth 16 can be so aligned as well. If desired, the circumference of the mouth 16 can be provided with a reinforced member or elastic member 20 to facilitate entry of and retention of the sleeve 14 on the stirrup 12. A pair of straps 22 will be integral with the outer surface of the sleeve 14 and contain inter-engaging fastening means 24, such as snaps, hook and eye, or the like to facilitate securely holding the sleeve 14 on the frame of the stirrup 12. It should be noted that the stirrup 12 is merely a frame having a central opening and therefore the sleeve 14 must neither fit too tightly nor too loosely since the pressure exerted by the heel will be transmitted thereonto such that a certain degree of play or pliability must be present.

If desired, a disposable cover portion 26 may be employed in conjunction with the sleeve 14 such that the latter 14 may be more or less permanently left on the stirrup 12 while the cover layer 26 is removed therefrom after each patient examination and a new one placed thereon. The cover layer 26 may be constructed of a non woven and have a "velcro" hooking layer 30 on one side thereof adapted to engage a "velcro" hook receiving layer 28 on the top surface of the sleeve 14, as shown in FIG. 2. For example, plastic hooks and hook engaging filaments, such as nylon tufts or the like. In this embodiment, the distal end 18 will also be out of planar alignment with the balance of the cover 26 for reasons of comfort.

Since it is obvious that numerous changes and modifications can be made in the above-described details without departing from the spirit and nature of the invention, it is to be understood that all such changes and modifications are included within the scope of the invention.

I claim:

1. A cover pad for the stirrup of a patient examination table, comprising a sleeve open at one end and defining a mouth for receiving said stirrup therein, at least the distal closed end of said sleeve being out of planar alignment with the remaining surface of said sleeve, a pair of straps disposed on said sleeve and adapted to contact one another whereby said sleeve may be tightened about said stirrup and fastening means disposed on said straps for securely engaging the same and a first layer of velcro disposed on one surface thereof, a planar removable cover layer substantially the same size as said sleeve and also including a second velcro layer thereon adapted to engage said first velcro layer whereby said sleeve remains on said stirrup and said cover layer is removed after patient examination.

2. The cover as defined in claim 1 wherein said mouth portion includes reinforcing means disposed about the circumference thereof.

3. The cover as defined in claim 1 wherein said mouth portion includes resiliant means disposed about the circumference thereof.

4. The cover as defined in claim 1 wherein said sleeve includes a vinyl layer on at least one surface thereof.

5. The cover as defined in claim 1 wherein said cover layer is a non woven.

* * * * *